United States Patent [19]

Fawzi et al.

[11] 4,406,884

[45] Sep. 27, 1983

[54] TOPICAL ANTIMICROBIAL COMPOSITION

[75] Inventors: Mahdi B. Fawzi, Fairfield; Melvin A. Barbera, Cincinnati, both of Ohio

[73] Assignee: The Procter & Gamble Company, Cincinnati, Ohio

[21] Appl. No.: 276,557

[22] Filed: Jun. 23, 1981

[51] Int. Cl.³ .................... A61K 31/19; A61K 31/20; A61K 31/78
[52] U.S. Cl. ..................................... 424/81; 424/317; 424/318
[58] Field of Search .......................... 424/81, 317, 318

[56] References Cited

U.S. PATENT DOCUMENTS

| | | | |
|---|---|---|---|
| 2,466,663 | 4/1949 | Russ et al. | 424/318 |
| 3,896,238 | 7/1975 | Smith | 424/358 |
| 4,018,918 | 4/1977 | Ayer et al. | 424/240 |
| 4,343,798 | 8/1982 | Fawzi | 424/240 |

FOREIGN PATENT DOCUMENTS 2912438 10/1980 Fed. Rep. of Germany .

OTHER PUBLICATIONS

Keeney, Bull, Johns Hopkins Hosp., 78, 333 (1946).

*Primary Examiner*—Leonard Schenkman
*Attorney, Agent, or Firm*—Steven J. Goldstein; Jack D. Schaeffer; Richard C. Witte

[57] ABSTRACT

Topical antimicrobial compositions in the form of an aqueous gel or lotion are disclosed; these compositions contain $C_5$–$C_{12}$ fatty acids and have a pH no greater than about 5. The compositions provide excellent broad-spectrum antimicrobial performance and, in fact, are more effective than similar compositions formulated as creams, ointments, non-aqueous lotions or non-aqueous gels. The method of treating skin disorders of pathogenic origin using these compositions is also disclosed.

13 Claims, No Drawings

TOPICAL ANTIMICROBIAL COMPOSITION

TECHNICAL FIELD

The present invention relates to topical pharmaceutical compositions, in the form of an aqueous gel or lotion, which exhibit outstanding antimicrobial properties.

BACKGROUND OF THE INVENTION

The use of antimicrobial agents plays an important role in current medical therapy. This is particularly true in dermatology where the most effective course of treatment for skin, mucous membrane, or hair lesions or infections frequently includes the use of a topical antimicrobial agent. The present invention is a topical antimicrobial composition, in the form of an aqueous gel or an aqueous lotion, which provides outstanding broad spectrum antimicrobial performance. The antimicrobial performance of the compositions of the present invention is superior to that of similar compositions formulated in a more conventional manner, such as creams, ointments, non-aqueous lotions or non-aqueous gels.

Various carboxylic acids are known to be effective antimicrobial agents; however, there is nothing in the art which would lead to the formulation of these compounds as aqueous gels or lotions, as opposed to more conventional product forms. Thus, for example, Keeney, *Bull. Johns Hopkins Hosp.*, 78, 333 (1946), teaches that sodium caprylate (sodium octanoate) is an effective fungistat, useful in the treatment of moniliasis. The sodium octanoate is taught to be useful in the form of an aqueous solution, ointment, jelly or powder, all of which have a pH of about 7.4. No general preference is taught for any one form of administration over another, except that the powder form is preferred over the jelly for vaginal use, since it is suggested to be less irritating. U.S. Pat. No. 2,466,663, Russ, et al., issued Apr. 5, 1949, teaches that mixtures of caprylic acid and caprylic acid salts are effective antimicrobial/antifungal agents over a wide pH range (pH=4.5-10.5). These compositions are taught to be useful topically when formulated in a variety of conventional ways having a pH within the broad useful range, the precise pH depending upon the particular physiological environment in which the compositions are to be applied. Finally, U.S. patent application Ser. No. 918,532, Stone, filed June 23, 1978, discloses the use of octanoic acid as a broad-spectrum antimicrobial agent in intravenous solutions. The antimicrobial benefits are taught to be optimal when the solution pH is kept in the range 3.5 to 6.0. There is no disclosure of the topical use of octanoic acid or of formulations for such usage in this patent application.

It is an object of the present invention to provide effective topical antimicrobial compositions containing $C_5$-$C_{12}$ fatty acids.

It is a further object of the present invention to provide effective topical antimicrobial compositions in the form of an aqueous gel or an aqueous lotion.

It is a still further object of the present invention to provide a method for the effective topical treatment of skin conditions of pathogenic origin.

SUMMARY OF THE INVENTION

The present invention provides topical pharmaceutical compositions in the form of an aqueous gel or an aqueous lotion, having a pH of no greater than about 5, comprising a safe and effective amount of an antimicrobial agent selected from $C_5$-$C_{12}$ fatty acids (especially octanoic or decanoic acid) and mixtures thereof.

In another aspect, the present invention provides a method for treating skin conditions of bacterial, yeast or fungal origin in humans or animals wherein a safe and effective amount of the compositions described above is topically applied to the afflicted situs.

DETAILED DESCRIPTION OF THE INVENTION

The phrase "safe and effective amount", as used herein, means sufficient fatty acid component or topical antimicrobial composition to desirably provide an antimicrobial effect, at a reasonable benefit/risk ratio attendant with any medical treatment. Within the scope of sound medical judgment, the required dosage of fatty acid or antimicrobial composition will vary with the nature and severity of the condition being treated, the duration of the treatment, the nature of adjunct treatment, the age and physical condition of the patient, the specific fatty acid being employed, and like considerations more fully discussed hereinafter.

"Pharmaceutically-acceptable", as used herein, means that the fatty acid compound and other ingredients used in the compositions are suitable for use in contact with the tissues of humans and lower animals without undue toxicity, irritation, allergic response, and the like, commensurate with a reasonable benefit/risk ratio.

The term "comprising", as used herein, means that various other compatible drugs and medicaments, as well as inert ingredients, can be conjointly employed in the compositions of this invention, as long as the critical fatty acid compounds are used in the manner disclosed. The term "comprising" thus encompasses and includes the more restrictive terms "consisting of" and "consisting essentially of".

By "compatible" herein is meant that the components of the present invention are capable of being commingled without interacting in a manner which would substantially decrease the efficacy of the fatty acids under ordinary use conditions.

All percentages and ratios used herein are by weight, unless otherwise specified.

The fatty acids useful in the present invention include those having from about 5 to about 12 carbon atoms; carboxylic acids outside of this range are significantly less effective as antimicrobial agents. These materials, themselves, are well-known in the art. For example, octanoic acid is an oily liquid having a boiling point of 239.7° C. and a melting point of 16.7° C.; it is very slightly soluble in water (0.068 g./100 g. at 20° C.) and freely soluble in alcohol, chloroform, carbon disulfide, petroleum ether and glacial acetic acid. Octanoic acid may be prepared from 1-heptene, DuPont, et al., *Compt. Rend.* 240, 628 (1955), or by the oxidation of octanol, Langenbeck, et al., *Ber.* 89, 202 (1956). The manufacture of octanoic acid is described in U.S. Pat. No. 2,821,534, issued in 1958 and assigned to GAF, and U.S. Pat. No. 3,053,869, issued in 1960 and assigned to Standard Oil of Indiana. See also *Fatty Acids*, Part 1, K. S. Merkley, ed. (Interscience, New York, 2d edition, 1960) pages 34, 38. Decanoic acid is a crystalline solid having a melting point of 31.4° C.; it is practically insoluble in water. See *Fatty Acids*, Part 1, supra, pages 34, 39. Decanoic acid may be prepared from octyl bromide, Shishido, et al., *J. Am. Chem. Soc.* 81, 5817 (1959), and U.S.

Pat. No. 2,918,494, issued in 1959 and assigned to Ethyl Corporation.

It is preferred that the fatty acid component be a $C_5$–$C_{12}$ non-aromatic carboxylic acid, such as n-pentanoic, n-hexanoic, n-heptanoic, n-octanoic, n-nonanoic, n-decanoic, n-undecanoic, or n-dodecanoic acid. Preferred fatty acid materials for use in the present invention contain from 6 to 10 carbon atoms, with octanoic and decanoic acids being particularly preferred. Mixtures of the above fatty acid materials may also be used, as may salts of the fatty acids, provided that pH criteria for the compositions, as described below, are met.

The fatty acid component is included in the compositions of the present invention in a safe and effective amount; preferably the compositions will contain from about 0.5% to about 20%, more preferably from about 1% to about 10%, of the fatty acid materials. The compositions are formulated to have a pH of no greater than about 5, preferably no greater than about 4, most preferably between about 3 and 4. At pH's above this range, the antimicrobial performance of the composition falls off significantly; obviously, a pH which is too low (acidic) would not be suitable for topical use. Compatible acidic or basic ingredients may be used to adjust the pH of the composition to the desired range.

The compositions of the present invention are formulated as aqueous lotions or aqueous gels; it has surprisingly been found that such aqueous lotion and gel compositions exhibit improved antimicrobial performance when compared with compositions containing the same antimicrobial agents formulated in more conventional ways, e.g., in the form of ointments, non-aqueous lotions, creams, or non-aqueous gels. Although not intending to be bound by theory, it is believed that the formulation of such aqueous gel or lotion compositions results in an aqueous phase supersaturated with the fatty acid (which has very low water solubility). This fact, coupled with the lipophilicity of the fatty acids, enhances the migration of the fatty acids from the aqueous phase of the composition to the skin.

Gels are transparent, semi-solid, colloidal systems where the water is restricted by an interlacing network of solvated particles. The gels useful in the present invention may have a wide range of viscosities, e.g., from about 4,000 to about 200,000 centipoise; however, since they are formulated for topical use, the compositions will generally have relatively high viscosities (i.e., they will be self-supporting).

The formulation of aqueous gels requires the presence of water and generally requires the use of a compatible pharmaceutically-acceptable gelling agent in the compositions of the present invention. Preferred compositions contain at least about 15% water, and may additionally contain an alcohol or mixture of alcohols (e.g., $C_1$–$C_{14}$) in a water:alcohol ratio of from about 5:1 to about 100:1. The gelling agent will generally be present at about 0.25% to about 10% of the composition. Desirable gels may be formed using an acidic carboxy polymer as the gelling agent, together with a compatible neutralizing agent. Pharmaceutically-acceptable acidic carboxy polymers include, for example, Carbopol compounds (a range of carboxy polymethylenes commercially available from B. F. Goodrich Chemicals, Cleveland, Ohio) and the neutralizing compounds include, for example, diisopropyl amine, sodium hydroxide, and beta-alanine. Surface active agents, especially nonionic surfactants, such as ethylene oxide/propylene oxide block copolymers (commercially available as Pluronics from BASF Wyandotte Corp.), and/or ethylene glycol or propylene glycol may also be included in the compositions to help in the formation of the gel and to act as dispersing agents for the active components. Preparation of gels is described in U.S. Pat. Nos. 4,018,918 and 4,257,908, both of which are incorporated herein by reference.

Aqueous lotions of the present invention are formulated in the same way as the above-described gels, except that they have lower viscosities (i.e., below about 4,000 centipoise) and do not include the gelling agent. Lotions are liquid preparations intended for external application to the skin. Most lotions contain finely powdered substances that are insoluble in the dispersion medium and are suspended through the use of suspending or dispersing agents. Other lotions have, as the dispersed liquid phase, liquid substances that are immiscible with the vehicle and are usually dispersed by means of emulsifying agents or other suitable stabilizers. The vehicles useful in the present invention are aqueous. Depending upon the nature of the ingredients, lotions may be prepared in the same manner as suspensions, emulsions or solutions. The fluidity of lotions permits their rapid and uniform application over a wide surface area. Pharmaceutical compositions in the form of gels and lotions are described in Ansel, *Introduction to Pharmaceutical Dosage Forms*, Lea & Febiger, Philadelphia, 1976, pp. 317–319 and 164–168, incorporated herein by reference.

The compositions of the present invention may additionally contain, at their art-established usage levels, compatible adjunct components conventionally used in the formulation of topical pharmaceutical compositions. These adjunct components include, but are not limited to, pharmaceutically active materials (such as supplementary antimicrobial or anti-inflammatory ingredients) or ingredients used to enhance the formulation, itself (such as excipients, dyes, perfumes, thickening agents, skin penetration enhancers, stabilizers, preservatives, and antioxidants). Particularly beneficial results are obtained when the compositions of the present invention contain a corticosteroid compound; such compositions are described in concurrently filed U.S. patent application Ser. No. 276,556, Fawzi, entitled "Topical Antimicrobial Anti-Inflammatory Compositions", incorporated herein by reference. The compositions of the present invention may also contain, in an amount which can range from about 1% to about 99.5% of the compositions, compatible pharmaceutical carrier materials especially adapted for topical application and formulation into an aqueous lotion or gel. Carrier materials suitable for use in the instant compositions include those well-known for use in the cosmetic and medical arts. Suitable carriers include, for example, water, liquid alcohols, liquid glycols, liquid polyalkalene glycols, liquid esters, liquid amines, liquid protein hydrolysates, liquid alkalated protein hydrolysates, liquid lanolin and lanolin derivatives, and like materials.

Topical treatment regimens according to the practice of this invention comprise applying a safe and effective amount of the compositions herein directly to the skin, e.g., at the situs of a skin condition of pathogenic origin or at a situs particularly susceptible to microbial contamination. The compositions may also be formulated for use in the oral or vaginal cavities. Conditions usefully treated with the compositions of the present invention include, but are not limited to, cutaneous candidiasis; superficial bacterial infections; the following conditions when complicated by candidal and/or bacterial infection: dermatitis (atopic, eczenatoid, stasis, nummular, contact or seborrheic), neurodermatitis, and dermatitis venenata; pruritus ani; pruritus vulvae; infantile eczema; and lichen simplex chronicus. The rate of application and duration of treatment will depend on the nature and severity of the condition, the response and physical condition of the particular patient, and related factors within the sound medical judgment of the attending physician. In general, for the compositions of the present invention, application rates of from 5 milligrams/cm$^2$ to about 100 milligrams/cm$^2$ per day are used. Application can be made once, or preferably several times, daily for periods of a week or more. In addition, the present invention may be formulated and used in veterinary practice, for example in the treatment of dermatological disorders characterized by inflammation and dry or exudative dermatitis, eczenatous dermatitis, contact dermatitis, seborrheic dermatitis, and as an adjunct in the treatment of dermatitis due to parasitic infestation.

The following examples illustrate the content, preparation and use of topical compositions of this invention, but are not intended to be limiting thereof.

EXAMPLE I

The antimicrobial efficacy of aqueous gel formulations of the present invention was compared to that of similar compositions formulated as creams, ointments and non-aqueous gels, using an in vitro disk diffusion test procedure. In this procedure, filter paper disks (11–13 mm diameter) were coated with the compositions to be tested and placed on top of agar media containing the microorganisms of interest. The agar was incubated (under conditions dictated by the particular microorganisms being used) overnight to allow the microorganisms to grow. As the test formulation diffused from the disk out through the agar, the growth of the microorganism was inhibited. Clear zones of inhibition were formed around the disks and were measured the following day. The size of the zone represents the degree of antimicrobial activity of the particular composition. The antimicrobial efficacy of the compositions was tested against *Candida albicans* (Candida), *Staphylococcus aureus* (Staph) and *Pseudomonas aeruginosa* (Pseudo). The compositions were tested both with and without a layer of synthetic sebum spread over the surface of the agar.

The compositions tested are summarized in the following table.

| Composition | Octanoic Acid | Triamcinolone Acetonide |
|---|---|---|
| 1 (aqueous gel) | 4% | 0.1% |
| 2 (cream) | 4% | 0.1% |
| 3 (ointment) | 4% | 0.1% |
| 4 (non-aqueous gel) | 4% | 0.1% |
| 5 (aqueous gel) | 4% | — |
| 6 (non-aqueous gel) | 4% | — |
| 7 (ointment) | 4% | — |
| 8 (cream) | 4% | — |

All compositions had a pH between about 3 and 4. The aqueous gel compositions included (vehicle) 1% myristyl alcohol; 25% propylene glycol; 5% Pluronic L-64; 1% beta-alanine; 25% of 4% aqueous Carbopol 934; with the balance being water. Conventional cream, ointment and non-aqueous gel bases were used for the remaining compositions. The antimicrobial performance of these compositions is given in the following table.

| | Zones of Inhibition (mm) | | | | | | | |
|---|---|---|---|---|---|---|---|---|
| | 1 | 2 | 3 | 4 | 5 | 6 | 7 | 8 |
| Candida | | | | | | | | |
| sebum | 29 | 22 | 19 | 18 | 26 | 19 | 21 | 23 |
| no sebum | 45 | 37 | 30 | 24 | 42 | 26 | 30 | 35 |
| Staph | | | | | | | | |
| sebum | 21 | 19 | 17 | 15 | 21 | 16 | 16 | 19 |
| no sebum | 33 | 32 | 24 | 20 | 34 | 20 | 24 | 30 |
| Pseudo | | | | | | | | |
| no sebum | 42 | 31 | 23 | 20 | 39 | 20 | 25 | 32 |

These data indicate that the compositions when formulated as aqueous gels of the present invention demonstrate clear antimicrobial performance advantages over similar compositions formulated as creams, ointments or non-aqueous gels.

Substantially similar results are obtained where the aqueous gel formulations, described above, are formulated as aqueous lotions by eliminating the Carbopol gelling agent.

Substantially similar results are also obtained where the octanoic acid in the above compositions is replaced, in whole or in part, with pentanoic, hexanoic, heptanoic, nonanoic, decanoic, undecanoic or dodecanoic acid, or mixtures thereof.

Similar results are also obtained where the triamcinolone acetonide in the above compositions is replaced, in whole or in part, with beclomethasone dipropionate, clobetasol propionate, diflucortolone valerate, fluocinolone acetonide, betamethasone benzoate, betamethasone dipropionate, betamethasone valerate, desonide, desoxymethasone, diflorasone diacetate, fluclorolone acetonide, fluocinonide, fluocortolone, fluprednidene (fluprednylidene) acetate, flurandrenolone, halcinonide, hydrocortisone butyrate, clobetasone butyrate, flumethasone pivalate, fluocortin butylester, hydrocortisone with urea, dexamethasone, hydrocortisone alcohol or acetate, methylprednisolone, or mixtures thereof.

EXAMPLE II

Using the disk diffusion procedure described in Example I, the antimicrobial efficacy of compositions of the present invention was tested. All of the compositions had pH's in the range of from 3 to 4. The compositions tested are described in the table below; in addition to the listed components all of the compositions were formulated as aqueous gels, containing 1% myristyl alcohol, 25% propylene glycol, 5% Pluronic L-64, 25% of 4% Carbopol 934 gelling agent, with the balance of the compositions being water.

| | Composition (weight %) | | | | | |
|---|---|---|---|---|---|---|
| Components | 1 | 2 | 3 | 4 | 5 | 6 |
| Octanoic Acid | — | — | — | — | 4.0 | 4.0 |
| Decanoic Acid | 4.0 | 4.0 | 6.0 | 6.0 | — | — |
| Triamcinolone Acetonide | 0.1 | 0.1 | 0.1 | 0.1 | 0.1 | 0.1 |
| Beta-alanine | 1.0 | — | 1.0 | — | 1.0 | — |
| 1 N NaOH | — | 7.0 | — | 7.0 | — | 7.0 |

The antimicrobial performance of each of these compositions, expressed as zone of inhibition diameters, over a range of gram positive and gram negative bacteria, both in the presence and absence of sebum, is summarized in the following table.

|  | Zones of Inhibition (mm) | | | | | |
|---|---|---|---|---|---|---|
|  | 1 | 2 | 3 | 4 | 5 | 6 |
| Staph | | | | | | |
| no sebum | 25 | 24 | 27 | 27 | 30 | 31 |
| sebum | 16 | 16 | 16 | 18 | 21 | 22 |
| Candida | | | | | | |
| no sebum | 21 | 21 | 24 | 20 | 38 | 38 |
| sebum | 0 | 0 | 0 | 0 | 28 | 25 |
| Pseudo | | | | | | |
| no sebum | 25 | 18 | 25 | 17 | 30 | 23 |

Similar results are obtained where the aqueous gel compositions, described above, are formulated without the Carbopol gelling agent, yielding aqueous lotion compositions.

EXAMPLE III

Using conventional pharmaceutical formulational techniques, antimicrobial compositions described in the following table were formulated as aqueous gels; each composition had a pH below 5.

non-aqueous gel bases were used in formulating the remaining compositions.

| | Compositions (weight %) | | |
|---|---|---|---|
| | Octanoic Acid | Triamcinolone Acetonide | Decanoic Acid |
| 1 (aqueous gel) | 4 | — | — |
| 2 (aqueous gel) | 4 | 0.1 | — |
| 3 (cream) | 4 | — | — |
| 4 (cream) | 4 | 0.1 | — |
| 5 (ointment) | 4 | — | — |
| 6 (ointment) | 4 | 0.1 | — |
| 7 (aqueous gel) | — | — | 4 |
| 8 (aqueous gel) | — | 0.1 | 4 |
| 9 (aqueous gel) | — | 0.1 | 4 |
| 10 (aqueous gel) | — | — | 4 |
| 11 (non-aqueous gel) | — | 0.1 | 4 |
| 12 (non-aqueous gel) | — | — | 4 |

The results of these tests are summarized in the following table. These data indicate that the addition of triamcinolone acetonide to the octanoic acid and decanoic acid aqueous gel, cream, ointment or non-aqueous gel compositions resulted in no antagonistic effects on their antimicrobial activity.

| Components | Composition (weight %) | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Octanoic Acid | 4.0 | → | → | → | → | → | → | → | → | → | → | → | → | → | → | → | → |
| Monolauren | 1.0 | → | → | → | → | → | → | → | → | → | → | → | → | → | → | → | → |
| Pluronic L-64[1] | 5.0 | | | | 5.0 | | | | | | 5.0 | | | | | | |
| Pluronic F-108 | | | | | 2.4 | | | | | | 2.4 | | | | 2.4 | | 2.4 |
| Pluronic F-127 | | 5.0 | | 2.5 | | | 5.0 | | 2.5 | | | 5.0 | | 2.5 | | 5.0 | |
| Pluronic F-123 | | | 5.0 | 2.5 | | | | 5.0 | 2.5 | | | | 5.0 | 2.5 | | | |
| Pluronic L-122 | | | | | 2.6 | | | | | | 2.6 | | | | 2.6 | | 2.6 |
| Propylene glycol | 20.0 | → | → | → | → | | | | | | 10.0 | → | → | → | → | → | → |
| Glycerin | | | | | | 20.0 | 20.0 | 20.0 | 20.0 | 20.0 | 10.0 | → | → | → | → | → | → |
| 1 N NaOH | 7.5 | → | → | → | → | → | → | → | → | → | → | → | → | → | → | → | → |
| Carbopol 934[2] | 1.0 | → | → | → | → | → | → | → | → | → | → | → | → | → | → | → | → |
| Water | 61.5 | → | → | → | → | → | → | → | → | → | → | → | → | → | → | 62.5 | 62.5 |

[1]Pluronics are a series of nonionic block-copolymer condensates of ethylene oxide with hydrophobic bases formed by condensing propylene oxide with propylene glycol, commercially available from Wyandotte Chemicals Corporation. For example, Pluronic L-64 has a molecular weight of about 2900 and an HLB of 15.0. Pluronic F-108 has a molecular weight of about 14,000.
[2]Carbopol 934 is a polyacrylic acid polymer available from B. F. Goodrich; it is soluble in water, polar solvents and many non-polar solvent blends.

These compositions, when applied topically to an adult human, in an amount of about 8 milligrams/cm$^2$, are effective antimicrobial agents. Using the disk diffusion procedure, described above, each of these compositions has been shown to be effective against *Staphylococcus epidermidis, Propionibacterium acnes, Candida albicans,* and *Pseudomonas aeruginosa.* Similar results are also obtained when a corticosteroid selected from the group triamcinolone acetonide, hydrocortisone acetate, betamethasone valerate, fluocinolone acetonide, and mixtures thereof is added to any of these compositions in an amount constituting about 0.025% to about 0.5% of the final composition.

EXAMPLE IV

Using the disk diffusion method, described in Example I, aqueous gel, cream, ointment and non-aqueous gel compositions, having the formulae given in the following table, were screened for their antimicrobial effectiveness. All of the compositions tested had pH's below 5. The aqueous gel compositions contained 1% myristyl alcohol, 25% propylene glycol, 5% Pluronic L-64, 1% beta-alanine, 25% of 4% Carbopol 934, with the balance being water. Conventional cream, ointment and

| | Zones of Inhibition (mm) | | | | |
|---|---|---|---|---|---|
| | Candida | | Staph | | Pseudo |
| | sebum | no sebum | sebum | no sebum | no sebum |
| 1 | 26 | 42 | 21 | 33 | 39 |
| 2 | 29 | 45 | 22 | 34 | 42 |
| 3 | 23 | 35 | 19 | 30 | 32 |
| 4 | 22 | 37 | 19 | 32 | 30 |
| 5 | 21 | 30 | 17 | 24 | 25 |
| 6 | 19 | 30 | 17 | 23 | 23 |
| 7 | 19 | 26 | 16 | 20 | 20 |
| 8 | 18 | 24 | 15 | 20 | 20 |
| 9 | 0 | 28 | 15 | 32 | 39 |
| 10 | 0 | 20 | 16 | 31 | 29 |
| 11 | 0 | 0 | 0 | 15 | 0 |
| 12 | 0 | 0 | 0 | 15 | 0 |

Substantially similar results are obtained where the octanoic or decanoic acids of the above compositions are replaced, in whole or in part, with equivalent amounts of pentanoic, hexanoic, heptanoic, nonanoic, undecanoic or dodecanoic acid, or mixtures thereof. Similar results are also obtained where the triamcinolone acetonide is replaced, in whole or in part, with effective amounts of hydrocortisone acetate, betamethasone valerate, fluocinolone acetonide, beclomethasone dipropionate, clobetasol propionate, diflucortolone valerate, betamethasone benzoate, betamethasone dipropionate, desonide, desoxymethasone, diflorasone diacetate, fluclorolone acetonide, fluocinonide, fluocortolone, fluprednidene (fluprednylidene) acetate, flurandrenooone, halcinonide, hydrocortisone butyrate, clobetasone butyrate, flumethasone pivalate, fluocortin butylester, hydrocortisone with urea, dexamethasone, hydrocortisone alcohol or acetate, methylprednisolone, or mixtures thereof.

EXAMPLE V

In order to compare the antimicrobial activity of octanoic acid/triamcinolone acetonide combinations against the activity of compositions containing three other corticosteroids at concentrations which are common in currently marketed products, the following compositions were screened using the disk diffusion procedure. All of the compositions were in the form of aqueous gels; these gel compositions contained (vehicle) 1% myristyl alcohol, 25% propylene glycol, 5% Pluronic L-64, 1% beta-alanine, 25% of 4% aqueous Carbopol 934, with the balance being water. All of the gel compositions had pH's between about 3 and 4.

Compositions (weight %)

1—0.05% triamcinolone acetonide
2—0.05% triamicinolone acetonide+4% octanoic acid
3—0.5% hydrocortisone-21-acetate
4—0.5% hydrocortisone-21-acetate+4% octanoic acid
5—0.1% betamethasone valerate
6—0.1% betamethasone valerate+4% octanoic acid
7—0.025% fluocinolone acetonide
8—0.025% fluocinolone acetonide+4% octaonic acid
9—vehicle (no active)

The results of these experiments are summarized in the table, below. In all instances, the corticosteroid alone showed no antimicrobial activity. All of the compositions containing 4% octanoic acid showed good activity. Zones of inhibition were approximately the same size for all of these compositions regardless of the steroid or its concentration.

| | Zones of Inhibition (mm) | | | | |
|---|---|---|---|---|---|
| | Staph | | Candida | | Pseudo |
| | sebum | no sebum | sebum | no sebum | no sebum |
| 1 | 0 | 0 | 0 | 0 | 32 |
| 2 | 21 | 34 | 25 | 40 | 39 |
| 3 | 0 | 0 | 0 | 0 | 31 |
| 4 | 23 | 35 | 27 | 39 | 39 |
| 5 | 0 | 0 | 0 | 0 | 29 |
| 6 | 20 | 36 | 25 | 46 | 38 |
| 7 | 0 | 0 | 0 | 0 | 30 |
| 8 | 22 | 37 | 27 | 44 | 38 |
| 9 | 0 | 0 | 0 | 0 | 29 |

What is claimed is:

1. A topical pharmaceutical composition in the form of an aqueous lotion or aqueous gel, having a pH no greater than about 5, comprising a safe and effective amount of an antimicrobial agent selected from the group consisting of $C_5$-$C_{12}$ fatty acids and mixtures thereof.

2. A composition according to claim 1 which contains from about 0.5% to about 20% of the antimicrobial agent.

3. A composition according to claim 2 in the form of an aqueous gel which contains from about 0.25% to about 10% of a gelling agent.

4. A composition according to claim 3 which additionally contains from about 1% to about 99.5% of a pharmaceutically-acceptable topical carrier.

5. A composition according to claim 4 wherein the antimicrobial agent is selected from the group consisting of $C_6$-$C_{10}$ fatty acids and mixtures thereof.

6. A composition according to claim 5 wherein the antimicrobial agent is selected from the group consisting of octanoic acid, decanoic acid, and mixtures thereof.

7. A composition according to claim 6 which contains from about 1% to about 10% of the antimicrobial agent.

8. A composition according to claim 6 wherein the gelling agent is an acidic carboxy polymer.

9. A composition according to claim 1 wherein the antimicrobial agent is selected from the group consisting of octanoic acid, decanoic acid, and mixtures thereof.

10. A composition according to claim 9 wherein the antimicrobial agent is octanoic acid.

11. A composition according to claim 1 having a pH no greater than about 4.

12. A composition according to claims 1 or 9 containing at least about 15% water.

13. A method of treating skin conditions of bacterial, yeast or fungal origin in humans or animals comprising the topical application to the afflicted situs of a safe and effective amount of the composition according to claim 1.

* * * * *